United States Patent [19]

Angelino-Pievani

[11] 4,429,690

[45] Feb. 7, 1984

[54] PLATE FOR BROKEN BONE FIXATION

[75] Inventor: Giancarlo Angelino-Pievani, Pioltello, Italy

[73] Assignee: Cise Centro Informazioni Studi Esperienze SpA, Italy

[21] Appl. No.: 295,469

[22] Filed: Aug. 24, 1981

[30] Foreign Application Priority Data

Sep. 15, 1980 [IT] Italy .............................. 24658 A/80

[51] Int. Cl.³ ............................................. A61F 5/04
[52] U.S. Cl. ................................ 128/92 D; 128/92 C
[58] Field of Search .............. 128/92 D, 92 C, 92 EB, 128/92 B, 92 R

[56] References Cited

U.S. PATENT DOCUMENTS

| | | | |
|---|---|---|---|
| 2,406,832 | 9/1946 | Hardinge | 128/92 D |
| 2,501,978 | 3/1950 | Wichman | 128/92 D |
| 2,580,821 | 1/1952 | Nicola | 128/92 D |
| 3,565,066 | 2/1971 | Roaf et al. | 128/92 D |

FOREIGN PATENT DOCUMENTS

| | | | |
|---|---|---|---|
| 451868 | 10/1948 | Canada | 128/92 D |
| 7393 | 2/1980 | European Pat. Off. | 128/92 D |
| 2131422 | 12/1971 | Fed. Rep. of Germany | 128/92 D |

Primary Examiner—C. Fred Rosenbaum
Assistant Examiner—C. W. Shedd
Attorney, Agent, or Firm—Karl W. Flocks; Sheridan Neimark

[57] ABSTRACT

A plate for the fixation of a broken bone comprises two longitudinal bars jointed by an array of humped bridges (cross-brackets) evenly spaced apart and having holes to house set cortical screws.

4 Claims, 4 Drawing Figures

PLATE FOR BROKEN BONE FIXATION

Surgical fixation of diaphyseal fractures by means of internal plates tends to replace the conventional method of applying a plaster cast.

The advantages achieved thereby are:

(a) Anchylosis of the articulations involved by the plaster cast is prevented;

(b) An early mobilization of the muscles close to the fractured area is obtained so that said muscles can be exercised and the occurrence of post-traumatic oedema is prevented, and (c) A reduction of the stay time as an in-patient is obtained.

However, many shortcomings are the result of the use of the plates as used nowadays, viz.:

(a) A poor resistance of the plate to accidental overloads, especially to transversal or torsion loads, and (b) A poor resistance of the plate to fatigue. The applied cyclical stress may be the result of muscular activity which, seemingly, does not load the limb, or of the patient walking with an improper use of the subsidiary supporting means, such as crutches and canes.

The facts outlined above are so important that many specialized Medical Centers restrict the use of such plates to quite rare and exceptional cases, and admit a great number of patients, coming from other Medical Centers, complaining plate failures. It must be observed that, while the application of a plaster cast originates a hazardous articular immobility recalled above, it affords, however, a considerable degree of protection (both from the physical and aesthetic and the psychological standpoint) to the offended limb and prevents the paitent from indulging in premature dangerous excerise, this possibility being the greater, the younger and the livelier the patient is.

In the present times, the plate which is most widely used in the treatment of bone fractures is the so-called Müller's plate, which consists of a slightly cambered metal plate having two sets of holes for holding cortical screws to be screwed into the bone on both sides of the fracture line. The number of holes is varied from 4 to 16 and the material which is used is AISI 316 L stainless steel workhardened by cold deformation until obtaining a yield point in the neighbourhood of 80 kg/mm$^2$–90 kg/mm$^2$. In the central zone, the moment of inertia of the plate, which works prevailingly under bending stresses, is more than satisfactory; whereas its value drops considerably at holes cross-section. The specific stress in the cross-sectional portion which contains the hole is much stronger than that experienced in the centeral zone, even if no account is taken of the stress intensity factor originated by the variation of the cross-sectional area in correspondence with the hole. It is not difficult, therefore, to forecast a low-cycle fatigue failure of the plate in correspondence with the cross-sectional zone which contains one of the two holes closest to the central zone. Further weak points of the plate can be found in correspondence with all the other holes: however, inasmuch as these are not subjected to considerable stresses they never become fracture-prone spots, so that the mechanical meaning of a plate having more than 6 holes is not easily understandable.

Tests have been conducted on Muml/u/ ller's plates by applying a pulsatory load on 180 kg at the frequency of 25 cycles per second (Hz) on a model of bone-plate junction. The fatigue failure has been produced after 200,000 cycles (equivalent to about 20 days of the use of the prosthesis) and exactly in the sectional zone aforementioned. These results are in agreement with fractures experienced on patients after 15 to 20-day walking.

An object of the present invention is to provide a plate of the kind referred to above which offers a high degree of mechanical robustness so as not to be fracture-prone as the conventional plates are, and more particularly the Muml/u/ ller's plates aforesaid: the shortcomings of the conventional plates as experienced hitherto can thus be done away with, or strongly reduced.

The object of the invention is achieved by a framework plate for jointing the ends of a broken bone, said plate being characterized in that it is composed by two parallel longitudinal bars which longitudinally mate on said bone ends to be fixed and are connected by a set of crosswise arranged bridging brackets cross-brackets) which are distributed at intervals along the length of said longitudinal bars, holes being provided through said cross-brackets for housing cortical screws intended to fix the plate to the bone to be setted.

In order that the features and advantages of the invention may be better understood, an exemplary embodiment thereof will now be described hereinafter, the description being aided by the accompanying drawing, wherein.

Figure 1:
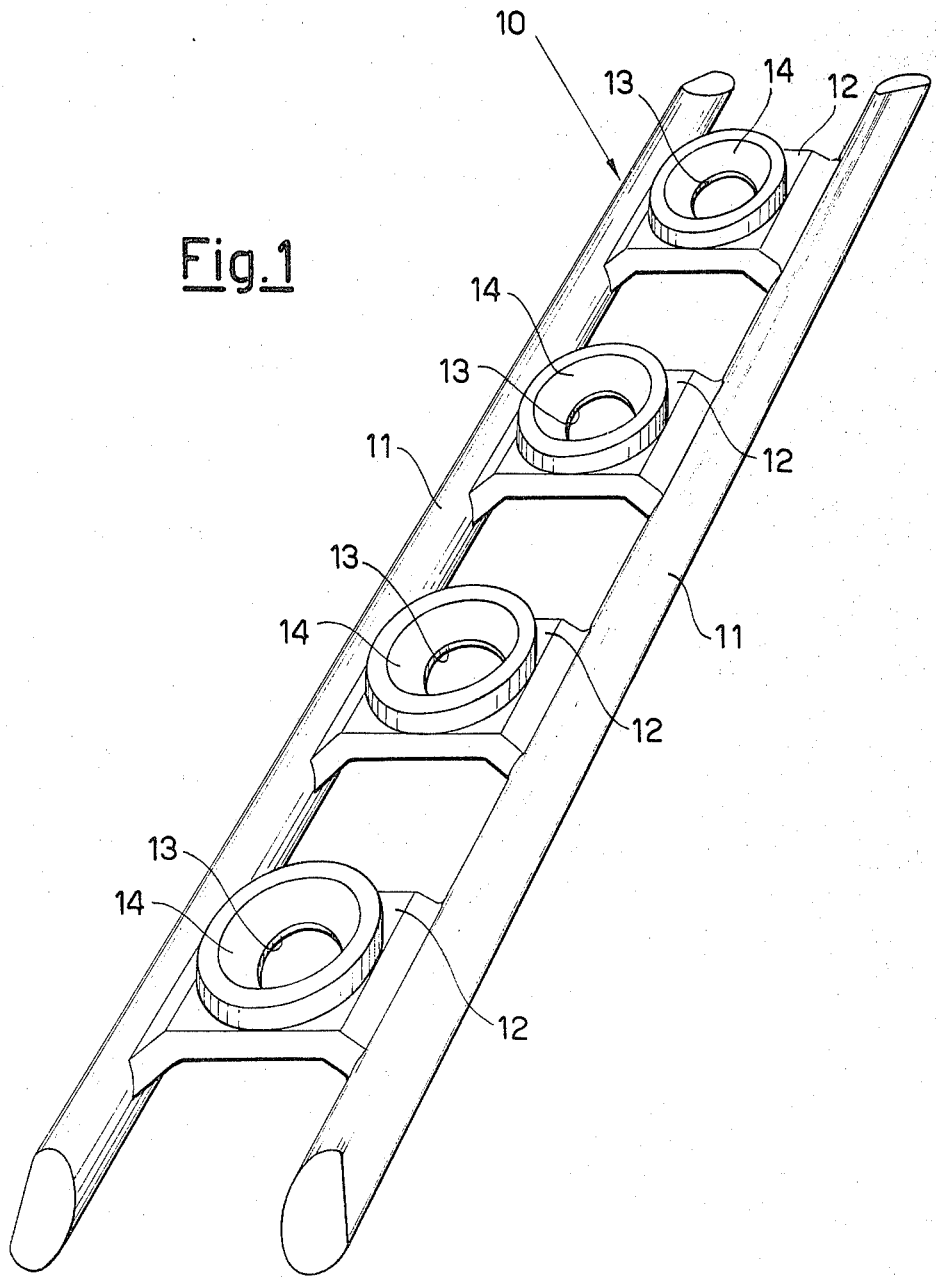
FIG. 1 is a perspective view of a plate according to the invention.

By way of example only, a plate according to the invention, generally shown at 10 (FIG. 1), essentially consists of two parallel longitudinal bars, 11, which are connected by cross-brackets 12 (four of them are shown in the drawing) which are arranged crosswise of the longitudinal bars and evenly spaced apart along the length of the two longitudinal bars 11 aforesaid.

Each longitudinal bar 11 has a cross-sectional outline substantially in the form of a circular segment and is intended to rest against the two bone stumps to be jointed.

Each cross-bracket 12 has a centrally positioned hole 13 which is countersunk as at 14: the hole 13 allows the screw 15 to pass therethrough to fasten the plate 10 to the broken bone and the countersink 14 provides slackless contact and room for the spherical head 16 of the screw 15 which enters the hole and bites into the bone mass. Each cross-bracket 12 is shaped like a bridge and is welded to the longitudinal bars 11 in such a position as the bottom surface of the cross-bracket 12 may never contact the bone surface once the plate 10 has been placed thereon.

Figure 3:
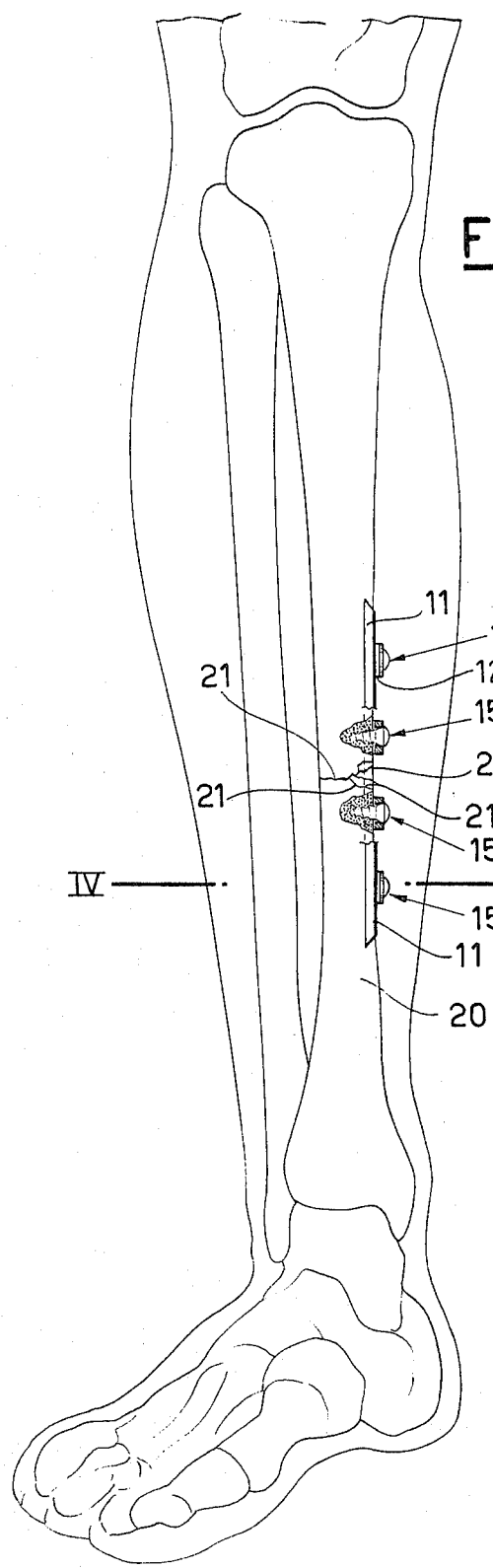
FIG. 3 is a diagrammatical view of the plate of FIG. 1 secured to a broken tibia.
Figure 2:
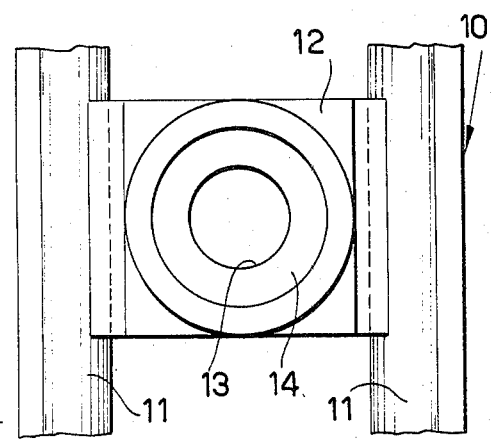
FIG. 2 is a partial plan view of the plate shown in FIG. 1.
Figure 4:
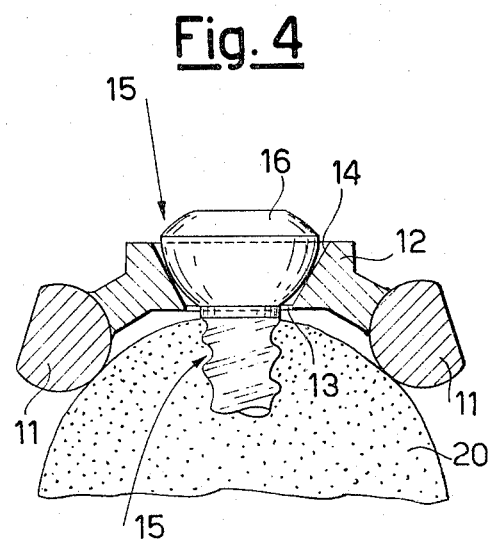
FIG. 4 is a cross-sectional view, taken along the line IV—IV of FIG. 3.

FIGS. 3 and 4 show a plate 10 placed on a human tibia 20 which has been fractured at 21. Two screws 15 secure the plate 10 above the fracture line 21 and two screws do so below the fracture line, so that the longitudinal bars 11 are urged against the bone surface.

According to the objects of the invention, a framework structure is obtained which has a high resistance to bending and twisting without having any restricted sections exposed to fatigue-failure in correspondence with the holes.

As a matter of fact, the bend-resisting members, i.e. the longitudinal bars 11, are not involved with the holes through which the screws are passed. The screw heads act upon the longitudinal bars through the intermediary of the cross-brackets 12.

It should not be overlooked, moreover, that the pressure on the bone surface, exerted along two generating lines which are comparatively widely spaced apart from one another, affords a great resistance, also against twists, to the limb while healing and the fracture of the bone is extremely efficiently immobilized. It must be evidenced that these advantages are achieved by using a plate radial size of which does not exceed that of the conventional plates, inasmuch as the plate of the invention wraps well around the bone surface. Also the bone-masking area has an extension which is quite comparable with that of conventional plates.

In the tests for simulating the stresses in the plate in working position, no case of failure by fatigue has been experienced even after a number of cycles corresponding to many months of use in walking.

In this connection, it should also be noted that possible failures by fatigue would, speculatively enough, be surmised in the bridge areas (midsection of cross-brackets), if any, and, if so, no sudden and total collapse would be experienced, contrary to what would occur with the conventional plates which when broken would in turn break the bone again.

Once the basic principle of the invention has been understood, it is apparent that a number of modifications and changes may be introduced therein for adapting the plate to the several requirements to be fulfilled in practical use.

Thus, the cross-sectional outline of the longitudinal bars 11 can be changed, even if it is appropriate that they have a convex outline in the portion intended to rest against the bone surface.

Likewise, the shape of the cross-brackets 12, and their positions and their numbers, shall be selected according to advisability both from the point of view of mechanical resistance, and the production technology to be adopted by the industry for producing the plate.

It is apparent that the spacing between cross-brackets, as well as their shape and curvature shall be commensurate with the cross-section shape of the bone to which the plate shall be applied in order that the bone may be correctly encompassed but without having the cross-brackets bottom surface being anywhere in contact with the bone.

Lastly, as far as the manufacturing technology is concerned, many appropriate methods can be adopted. For example, it is quite possible to prepare the plate by machining from a work-hardened stainless steel, such as AISI 316 L, or by powder sintering (cobalt, chromemolybdenum alloys), or by cold or hot-pressing of sheet products (stainless steel or titanium alloy).

I claim:
1. A plate for treatment of bone fractures by joining parts of a broken bone across the fracture line by screw attachment to the parts to be joined comprising
   a framework plate including
      a pair of longitudinal bars having convex undersurfaces supporting said framework plate while lying in a longitudal direction along the broken bone with each of said bars supported on opposite sides of the fracture in said broken bone,
      a plurality of cross-bracket bridging members with each of said members integrally connected to each of said longitudinal bars and extending therebetween, said cross-bracket bridging members spaced along said longitudinal bars and from each other with open spaces therebetween,
      each of said bridging members having a hole therethrough for holding a screw for attachment to a bone part.
2. The plate of claim 1 wherein
each of said bridging members form generally an arch between said longitudinal bars which raises the bottom surface said members between said bars above the bone surface portion encompassed by said longitudinal bars whereby contact by the bottom surface with the bone surface portion is avoided.
3. The plate of claim 2 wherein
said longitudinal bars each have a solid rod cross-section.
4. The plate of claim 2 wherein
each of said holes in said bridging members is countersunk in said bridging member.

* * * * *